United States Patent [19]
Alt et al.

[11] Patent Number: 6,080,187
[45] Date of Patent: Jun. 27, 2000

[54] CARDIAC PACEMAKER WITH BIDIRECTIONAL COMMUNICATION

[75] Inventors: Eckhard Alt, Ottobrunn, Germany; Lawrence J. Stotts, Lake Jackson, Tex.

[73] Assignee: Intermedics Inc., Angleton, Tex.

[21] Appl. No.: 09/055,212

[22] Filed: Apr. 6, 1998

Related U.S. Application Data

[62] Division of application No. 08/733,552, Oct. 21, 1996, Pat. No. 5,792,205.

[51] Int. Cl.⁷ ..................................... A61N 1/368
[52] U.S. Cl. ................................................. 607/32
[58] Field of Search ................... 607/30, 32, 60, 607/4, 5, 36; 128/903

[56] References Cited

U.S. PATENT DOCUMENTS

| | | | |
|---|---|---|---|
| 4,295,474 | 10/1981 | Fischell | 600/510 |
| 4,481,950 | 11/1984 | Duggan | 607/29 |
| 5,040,533 | 8/1991 | Fearnot | 607/22 |
| 5,076,272 | 12/1991 | Ferek-Petric | 607/28 |
| 5,549,653 | 8/1996 | Stotts et al. | 607/4 |
| 5,556,421 | 9/1996 | Prutchi et al. | 607/36 |
| 5,607,459 | 3/1997 | Paul et al. | 607/29 |
| 5,609,614 | 3/1997 | Stotts et al. | 607/29 |
| 5,609,615 | 3/1997 | Sanders et al. | 607/36 |
| 5,620,475 | 4/1997 | Magnusson | 607/30 |

Primary Examiner—Jeffrey R. Jastrzab
Attorney, Agent, or Firm—Schwegman, Lundberg, Woessner and Kluth

[57] ABSTRACT

An interventional medical device has a capability to sense cardiac dysrhythmias and to selectively respond with one among a hierarchy of therapies appropriate to terminate the sensed dysrhythmia and return the heart of the patient in whom the device is adapted to be implanted to normal sinus rhythm. The device includes a therapy generator having a housing and electronics for conducting bidirectional communication with the patient. The bidirectional communication is carried out by detecting the occurrence of a predetermined dysrhytlnia, such as atrial fibrillation, to alert the patient of such occurrence, and by responding to instructions from the patient following such alert for addressing the detected predetermined dysrhythmia. The detection is performed by electrodes mounted directly on the header of the device housing to both detect occurrence of the atrial fibrillation and for alerting the patient thereof by stimulating body tissue such as pectoral muscle in the vicinity of the header electrodes. Response to patient-initiated instructions is implemented by triggering certain device functions such as storage of ECG events detected by the header electrodes, or deliver of a therapy appropriate to terminate the atrial defibrillation, or delay of delivery of the appropriate therapy, according to the nature of the patient-initiated instructions.

20 Claims, 3 Drawing Sheets

CARDIAC PACEMAKER WITH BIDIRECTIONAL COMMUNICATION

CROSS-REFERENCE TO RELATED APPLICATIONS

This is a divisional application of U.S. application Ser. No. 08/733,552 filed Oct. 21, 1996 now U.S. Pat. No. 5,792,205.

BACKGROUND OF THE INVENTION

The present invention relates generally to cardiac pacing, and more particularly to an implantable cardiac pacemaker which is implemented with the capability to provide bidirectional communication not only with a programmer or telemetry receiver external to the patient's body but with the patient himself.

Cardiac pacemakers generally provide means for sensing electrical signals generated by the heart to control the stimulation of excitable tissue in the chambers, and for sensing the cardiac response to such stimulation (e.g., intracardiac signals), and means for responding to an inadequate or inappropriate stimulus or response (e.g., dysrhythmia) to undertake delivery of therapeutic stimuli to the patient's heart. This generalized function exists regardless of whether the implanted device is intended for pacing alone or has additional capabilities of cardioversion or defibrillation, to alleviate other dysrhythmias such as pathologic tachycardia or fibrillation.

A current matter of concern in cardiac pacemakers resides in the safety of pacer interaction with the patient. Despite improved cardiac pacemaker technology, the pacemaker patient may still suffer from symptoms of an underlying cardiac disease after the pacemaker has been implanted. For example, the patient may experience a symptomatic, unpleasant, irregular heartbeat. The attending physician must evaluate the symptoms and diagnose their underlying cause. A reliable evaluation, however, may be frustrated by the fact that the symptoms occur only infrequently. That is to say, the patient may be event- and symptom-free for a substantial period of time, e.g., several months; but at some point in time the previously suffered unpleasant symptoms may recur. 24-hour monitoring of the patient is not a viable solution in these circumstances because the likelihood of detecting such a sporadic rhythm disorder is extremely low. But a technique of recording the patient's intracardiac signal from time to time or which is triggered upon the occurrence of a certain rhythm disorder could be fruitful.

Reliable detection of the intracardiac signal requires that the electrode(s) must have and maintain proper electrical contact with the tissue of the heart, and that the device leads are operating properly. Such detection will be frustrated or may fail entirely in the event of failure of a lead, such as an incomplete lead fracture which results in only intermittent loss of signal, or a defect in the lead insulation, or improper placement of the electrode that results in unreliable contact with myocardial tissue in the chamber of interest. In such cases, it would be helpful to have available a real-time electrocardiogram (ECG) signal or chart that is not restricted to endocardial information derived from the pacing (or other function) leads. Of course, a surface electrocardiogram would provide alternative or additional verification of the status of the patient's cardiac activity and the operation of the implanted pacemaker, but such an alternative is not particularly viable where the patient is suffering from symptoms attributable to intermittent failures of the implanted pacemaker.

It is a principal aim of the present invention to provide an implantable cardiac pacemaker or other implantable cardiac therapeutic medical device which is capable of detecting or permitting the detection of faults in the implanted lead system associated with the device or the device itself, and which is implemented to do so in a simple and low cost manner. An additional objective is to provide means for alerting the patient to a problem in the implanted system and/or to more readily enable the patient to take manual action to temporarily override certain operations of the implanted device in response to cardiac dysrhythmias which are not life threatening.

The implanted pacemaker may be implemented to perform other functions as well, such as cardioversion and defibrillation. Such multi-function implantable medical devices are well known. In the instance of a device which is capable of detecting atrial fibrillation, such fibrillation will be detected by the device but may not be sensed by the patient himself. Indeed, this is a frequent occurrence. Generally, implantable devices which detect atrial fibrillation are implemented to deliver a defibrillating shock to the atria, which can be painful to the patient. Atrial fibrillation is not an immediate life-threatening disorder, but if left untreated for 24 to 48 hours the patient will require anticoagulation (i.e., the administering of an anticoagulant agent such as heparin or hirudin into the bloodstream) to avert the possible development of a resulting embolism or thrombus in the affected chamber which could lead to a myocardial infarction or stroke.

If given a choice, the patient suffering atrial fibrillation might well elect, nevertheless, to put off the shock until such time as he or she is resting, or is in a situation which is more convenient for acceptance of a shock applied to the heart. For example, the patient might be on a long drive when the atrial fibrillation occurred, at a time when a shock could cause a loss of control of the vehicle. The first problem then is for the patient to be aware of the atrial fibrillation, which, as pointed out above, is often unobserved except by an implanted device that would deliver an automatic shock; and the second problem is to give the patient an opportunity to possibly defer the defibrillating shock, at least briefly, to a more propitious time to receive treatment for the disorder.

Therefore, it is another aim of the invention to provide means for notifying the patient when an attack of atrial fibrillation occurs, before delivery of a shock as the automatic therapy delivered to treat the disorder, and to provide a way in which the patient can adjust the timing of the shock, within limits, according to the patient's convenience.

SUMMARY OF THE INVENTION

Briefly, the present invention resides in an implantable cardiac therapeutic medical device which is provided with tiny external electrodes on the case of the signal generator (alternatively referred to herein as the stimulus generator or pulse generator), preferably in the region of the insulative header. The electrodes, which are disposed flush with the surface of the header (i.e., are surface-mounted) as tiny dots of electrically conductive material electrically connected via an insulated feed-through aperture (or apertures) to an appropriate node (or nodes) of the internal electrical circuitry of the generator, are arranged to detect the electrical signals that spread through the patient's body from cardiac activity. Additionally, these small electrodes exposed at the surface of the case may be used to stimulate the patient's muscle tissue adjacent to the implant site, to indicate the existence of a problem in the pacemaker operation, or to warn the patient of the onset of a disorder such as atrial fibrillation.

The present invention, therefore, comprises means in the form of device surface-mounted electrodes to derive additional ECG information independent of the implanted pacemaker leads, and to obtain from the patient's underlying cardiac rhythm, information which may be used to alert a patient of the existence of an arrhythmia or a malfunction in the device operation. The surface-mounted electrode-based information may be transmitted in parallel with the pacemaker lead-based ECG information to facilitate diagnosis of a possible lead failure, and to enhance the differentiation between a device- or lead-based problem and an actual arrhythmia.

Device malfunctions may include battery depletion, loss of capture, increase in impedance, decrease in impedance below a certain level, and, in general, any irregularity relative to a pre-defined range of normal functions. Lead malfunctions may include intermittent failure caused by wire fracture, or deterioration of lead insulation, and so forth. The patient can be alerted to a detected malfunction by periodic stimulation of the pectoral muscle (or other tissue depending on the implant site) through application of a voltage in the range from 2.0 to 7.5 volts to the surface-mounted electrodes. The patient will sense this definitive muscle twitching, and from prior discussion of the peculiar characteristics of this device capability with the physician, will recognize it as indicative of a device/lead problem calling for physician contact and intervention with all due dispatch. The stimulation itself may be coded, as by particular patterns of the stimuli, so that the patient can discriminate between a detected device malfunction and the presence of a dysrhythmia such as atrial fibrillation which requires treatment. In one instance, the patient would immediately ask the physician to verify proper performance of the implanted device and associated lead(s); and in the other instance, the patient has the option to postpone delivery of a shock from the device for a limited period of time. Instead of muscle stimulation, an acoustic source in the device housing may be used to alert the patient to a problem by sounding an audible alarm such as distinctive beeps.

Preferably, the muscle is stimulated by application of low level stimulating pulses to the surface-mounted electrodes in a patterned sequence to allow the patient to recognize these distinctions. Also, the device preferably responds in a distinct way to a pattern of taps by the patient (by drumming a fingertip or knuckle at the implant site) to cease the stimulation, or postpone a shock, or deliver a shock at a time more appropriate to the patient. Of course, the number of possibilities must be limited so that the patient is not likely to become confused or unprepared to take appropriate action. Hence, a device with such capabilities would not be prescribed by the physician for a patient whose medical problems include a diminished capacity, such as one suffering from Alzheimer's disease. The device is preferably provided with a fail-safe capability, such as periodic return to an earlier-interrupted original muscle stimulation pattern to avoid the unlikely event that the patient might have forgotten the earlier warning, or the delivery of a defibrillating shock in response to atrial fibrillation that has persisted for a preset interval of time, despite the patient having previously delivered a coded signal (through taps on the implant site) to temporarily defer the shock. Additionally, the device is arranged and adapted such that the turning off of one warning stimulus would not affect any other, so that if a different problem were to occur while a first had been noted by a muscle stimulation that was released by a signal from the patient, the warning indicia for the second problem would still get through.

The tapping by the patient is detected by a mechanical sensor or mechano-electrical transducer mounted inside the device case, to produce an electrical signal that may be processed by the device circuitry to yield the desired effect. For example, the transducer may be an accelerometer. If the device includes the capability of rate adaptive activity pacing, an accelerometer may already be present to detect patient activity and respond with an appropriate pacing rate. Processing circuitry would be used to distinguish the patient's coded tapping from signals indicative of activity such as walking.

It is desirable that real-time ECG information regarding the detected arrhythmia be available so that the physician can properly diagnose or analyze the problem. Ideally, given the constraints on device size and memory capacity of an implantable device with the current state of the art, this translates to limited telemetry or storage of critical data within the device for readout and recording on request. According to another aspect of the invention, storage and transmission of the ECG phenomena of interest may be achieved by either of two alternative methods. One is to store on a first in/first out data moving window basis, in a short term loop with a time-stamped selected interval of particular interest. Alternatively, the pertinent ECG information is frozen in storage by patient-initiation of the storage process through a coded sequence of tapping on the device at the implant site. The activating signal is coded to be readily distinguished from device detection of regular physical exercise, for example, so that such device response will not take place or is unlikely to be prompted as a consequence of normal patient activity.

Accordingly, it is another important aim of the present invention to provide an implantable medical interventional device which has the capability to enter into bidirectional communication with the patient by detecting cardiac signals that normally emanate through the body, distinct from the detection of intracardiac signals by pacing leads, as a potential check on the functionality of the pacing lead system and the device, as well as to confirm a dysrhythmia, and for automatic or manual activation of a storage instruction to record time-stamped signal information from which to analyze a device malfunction or a dysrhythmia.

BRIEF DESCRIPTION OF THE DRAWINGS

The above and still further, aims, objectives, aspects, features, and attendant advantages of the invention will become apparent from a consideration of the following detailed description of the best mode presently contemplated for practicing the invention, by reference to a preferred embodiment and method, taken in conjunction with the accompanying drawings, in which.

DETAILED DESCRIPTION OF THE PRESENTLY PREFERRED EMBODIMENTS AND METHOD

In a preferred embodiment of the invention, the header of the interventional medical device signal generator carries at least two small surface electrodes, such as titanium or iridium oxide dots which may be only a few millimeters (mm) in diameter, preferably 3 mm, embedded in the epoxy resin or other biocompatible insulative material of the header but exposed at its surface. Electrical connection is made from the surface electrodes using conductive leads via a conventional feed-through to the internal electrical circuitry of the device. Where the device is a cardiac pacemaker (including a multi-function device such as incorporating cardioversion and defibrillation therapy regimens), an electric field spreads through the body with depolarization of the heart, that may be detected by the surface-mounted electrodes to produce an ECG signal that may then be processed by the internal circuitry of the device. Two such dot electrodes will permit differential detection of the underlying rhythm.

The pacemaker case or an additional electrode may be used as a ground electrode to provide greater signal stability than is attainable with mere bipolar differential ECG detection, by eliminating noise accompanying detected signals through a type of common mode rejection. Clean detection of the atrial signal and proper recognition of the P-wave are important to detect arrhythmias that in many cases arise from atrial disorder. In patients with sinus node disease, one in every three to four patients exhibits intermittent atrial tachyarrythmias, such as atrial flutter, sinus tachycardia or atrial fibrillation. The additional surface-mounted electrodes also enable detection of the QRS-complex and the T-wave. The cardiac signal detected by the dot electrodes may be transmitted from the pacemaker via conventional telemetry as an ECG independent of the lead-based intracardiac ECG for display on a strip-chart recorder associated with an external programmer console.

Since the field or vector of the ECG which is to be detected by the two or three surface-mounted electrodes (possibly including the case) has a strength or magnitude which is direction-dependent, the signal generator of the device may be appropriately oriented when implanted in the patient by the surgeon, or may subsequently be programmed with the use of three poles for the electrodes, to optimize the field detection and, thereby, obtain a very clear and informative ECG.

Figure 1:
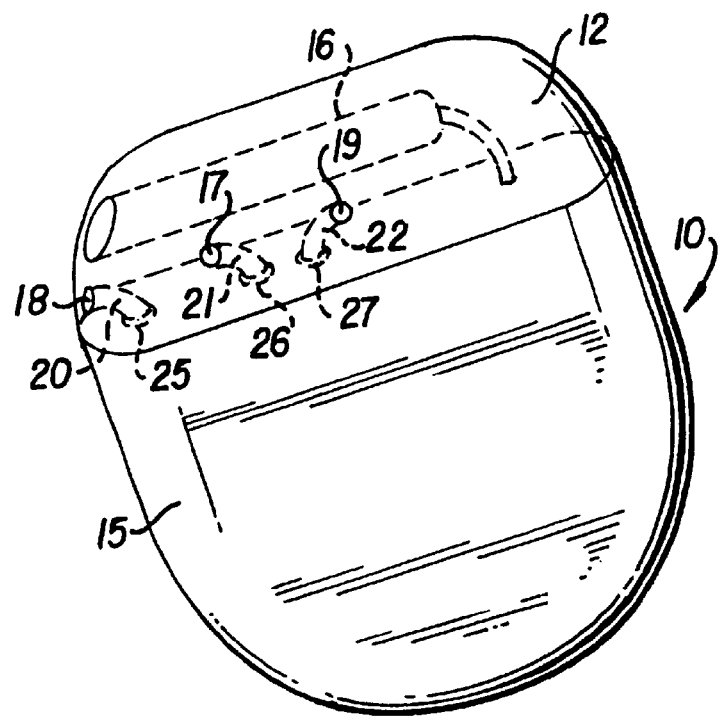
FIG. 1 is a front view, in perspective, of the exterior of a signal generator case of the device to be implanted in the body of a patient.

The implantable device of the invention, which may for example be a cardiac pacemaker/cardioverter/defibrillator, comprises a signal generator or stimulus generator 10 illustrated in perspective view in FIG. 1. The signal generator includes an electrically insulative header 12, which is illustrated as being transparent, and a conductive metal case 15. Both header and case are composed of conventional biocompatible materials so as to avoid adverse effect on the tissue and fluids of the body after implantation in the patient. The case 15 houses internal batteries (not shown) to power the device, and electrical circuitry (not shown) designed to perform conventional sense signal processing and the functions required of the therapy selected in response to sense signals indicative of dysrhythmias to be treated. Molded within the header 12 is an electrical female connector or connectors 16. The latter are designed to mate with the connector(s) at the proximal end of one or more leads (not shown) having electrodes positioned at the distal end thereof for interaction with the tissue of the heart when the device is operational after lead implantation by the surgeon in proper position in the patient's body.

According to a principal aspect and feature of the invention, the header 12 incorporates at least two and preferably three relatively tiny, spaced apart, surface-mounted intracardiac dot electrodes 17, 18, 19, each measuring about 3 millimeters (mm) in diameter, for example, and embedded in the insulative resin, such as epoxy resin, of the header so that a surface of each such electrode is relatively flush with the surface of the header, and thus with the surface of the signal generator case 15. The case preferably serves not only as the housing for the circuitry and the batteries of the pacemaker, but as a ground reference for the device operation. Alternatively or additionally, one surface-mounted dot electrode, e.g., 18, acts as electrical ground to provide a reference electrode for the detection process. These dot electrodes may be designed and arranged to enable bipolar differential detection of the patient's ECG signals, and preferably have a composition or surface layer of iridium oxide or titanium.

The surface mounted dot electrodes are configured on the header 12 in the manner illustrated in FIG. 1. Preferably, two of the electrodes 17 and 19 are located on opposite sides of the header, and are thereby spaced-apart by a distance defined by the thickness of the header. Each of these two of the surface-mounted electrodes is connected via its respective conductive wire 21 and 22, to predetermined nodes of the internal electrical circuitry of signal generator 10. The connecting wires are fed into (and from) the case via feed-through terminals 26 and 27, respectively, which allow conductive access between the header and the circuitry within the case while retaining the wires against electrical shorting. The surface-mounted electrodes are intended to sense the intracardiac signals that establish an electric field which spreads through the patient's body, independently of the cardiac signals sensed by distal and/or otherwise located electrode(s) on endocardial pacing lead(s) (not shown) connected to internal circuitry of the signal generator by connector 16.

The two electrodes 17 and 19 are also for stimulating muscle tissue adjacent the implant site of the signal generator, and are electrically connected to internal circuitry of the generator accordingly, to alert the patient of detecting a predetermined dysrhythmia. By locating them at opposite sides of the header, muscle stimulation will be achieved by energization from at least one of the two irrespective of which side of the signal generator case is implanted adjacent the pectoral muscle (i.e., whichever side may be planted facing "downward" (or inward) toward that muscle. The third surface-mounted dot electrode 18 is preferably arranged to lie between and be equally spaced-apart from the first two, albeit possibly offset from the line between them, for use as a ground or floating reference electrode to eliminate noise from the detected body cardiac signals by a form of common mode rejection. That electrode is connected by conductive wire 20 to a selected node of the internal circuitry via feed-through 26, but the case 15 may be used alternatively for the ground connection.

Figure 2:
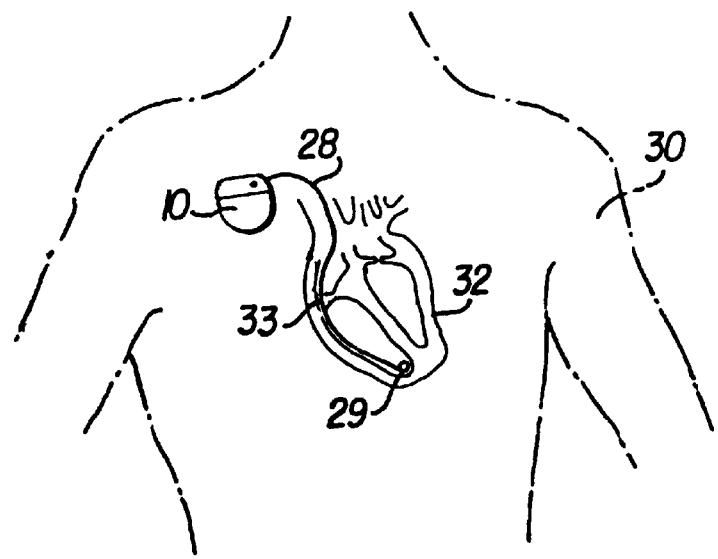
FIG. 2 is a partial front view of a patient, shown in phantom, illustrating the positioning of the implanted device.

FIG. 2 is a front view of a patient 30, shown in phantom, illustrating pacemaker signal generator 10 implanted, by way of example, at a site in the right side of the patient's chest. An endocardial lead 28 is connected at its proximal end to the generator and has its distal end threaded through the patient's superior vena cava (SVC) into the right atrium and through the tricuspid valve to position an electrode 29 at the distal end at the apex of the right ventricle of the patient's heart 32. An intermediate electrode 33 on lead 28 may be positioned for contact with myocardial tissue in the right atrium. Lead 28 carries separate insulated conductive wires from the respective electrodes thereof so that the electrodes are connected to electrical circuitry internal to the signal generator 10 through connector 16 of header 12. The lead electrodes are intended to be used for sensing cardiac activity of the patient's heart and to deliver electrical signals indicative thereof to the signal generator's sense amplifier and other processing circuitry (not shown), and, as well, to deliver stimulating, cardioverting, and/or defibrillating pulses from the signal generator's variable rate pulse generator to the respective chambers for pacing the heart according to a particular one of the various therapy protocols which are programmed in a conventional way into the signal generator.

The pacemaker signal generator 10 is implanted in a pocket formed by incision just below the flesh in the chest of patient 30, and, as noted above, will be positioned with one of the two surface-mounted electrodes 17, 19 facing inwardly of the body, adjacent the pectoral muscle, regardless of which side faces inward. This orientation also provides the device with greater sensitivity to the ECG signal information to be picked up, and greater assurance of pectoral muscle stimulation when a pacemaker (signal generator or pacing lead) problem, or a particular dysrhythmia (e.g., atrial fibrillation), causes the generation of a coded sequence of stimulating pulses by the signal generator and application of those pulses to the surface-mounted electrodes.

To that end, the pulse generator within generator case 15 is implemented in any conventional way to generate very low energy pulses in a distinctive pattern to identify the specific problem at hand. For example, if an intermittent shorting of the lead is detected, the pattern might be a sequence of three pulses equally spaced by a short interval followed by another pulse separated by a longer interval from that of the first three. In contrast, detection of atrial defibrillation might be set to produce two rapid pulses followed after a longer interval by two more rapid pulses, and so forth. These pulses are delivered to at least two of the three surface-mounted electrodes to cause an electrically stimulated twitching of the left pectoral muscle, which is easily sensed by the patient in the same code as the respective pulse sequence. This alerts the patient to the problem and its nature, to prompt a telephone report to the physician as well as schedule a visit for analysis and diagnosis. Alternatively, detection of such a problem or dysrhythmia may be used to generate coded pulses for application to a beeper 36 within case 15, such as a piezoelectric membrane, to sound an audible warning to the patient.

During implant, the generator case 15 may be oriented by the physician for optimum detection of the ECG signals by the surface-mounted dot electrodes 17, 18, 19. Conventional noise rejection serves to provide ECG signal information which is relatively clean and uncluttered to the detection circuitry within generator 10.

Figure 3:
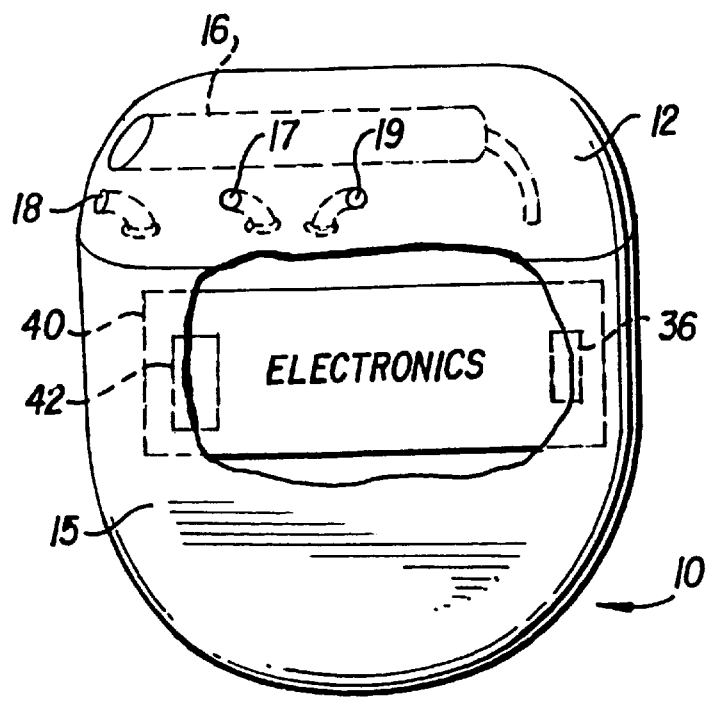
FIG. 3 is a fragmentary front view of the stimulus generator case focusing on the location of the dot electrodes in the header, and their connection to internal circuitry via wires passed through respective feed-through terminals between the case and the header.

In the cut-away front view of signal generator 10 illustrated in FIG. 3, the wires 20, 21, and 22 connected to surface-mounted electrodes 17, 18, and 19, respectively, are shown as being fed for connection to appropriate points of conductive paths at the side of a printed circuit (PC) board or other type of motherboard 40 that carries various integrated circuit components and other elements to implement the functions of the internal circuitry. It is sufficient to observe at this point that an accelerometer 42 is provided in the case and electrically connected to appropriate circuitry node(s) on the board to generate and deliver electrical signal information related to movements indicative of physical activity of the patient. In this embodiment, for example, the pacemaker is a rate-adaptive or rate-responsive device that adjusts its pacing rate according to patient activity. As will be described below, the accelerometer is also useful to respond to the patient's light taps on the implanted signal generator (by tapping on the skin over the implant site) to initiate a memory function in the device by which the detected ECG signal information, either or both (preferably, both) of the lead-based intracardiac signal and the surface-mounted electrode-based body cardiac signal, is recorded for ultimate transmission to a strip chart recorder for analysis.

Figure 4:
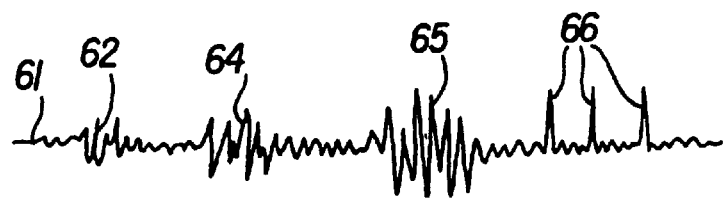
FIG. 4 is a chart generally illustrating differences between activity signals and patient-initiated tapping signals detected by an accelerometer in the device.

FIG. 4 illustrates activity signals from forces on the accelerometer indicative of an at rest condition 61, and of successive low activity 62, moderate activity 63, and greater activity 63 sessions, separated by brief periods of return to inactivity. In contrast, when the patient senses a particular pattern of muscle twitching representative of, say, atrial fibrillation, he may choose to postpone delivery of a defibrillating pulse to the atrium from the device. To that end, the patient would strike the implanted pacemaker in a stacato of, say, three short uniform, high amplitude, equally-spaced apart taps 66. The form of the latter signals is quite different from that of activity signals (albeit that the mere striking of the generator produces a microcosm of an activity signal), and, coupled with the coded pattern, the tap signals are readily distinguishable by detection circuitry to prompt the interruption of the process for generating, and thereby the postponement of, a defibrillating shock from the signal generator. The tap signals are readily detected as having certain characteristics of frequency content, amplitude, and duration for that purpose.

In the alternative, the patient may use a magnet 65 which is passed over the implanted housing of the therapy generator in a manner to induce initiation of a particular device function, such as real-time storage of the ECG event detected by the surface-mounted dot electrodes, or delivery of the appropriate therapy to terminate a detected dysrhythmia, or to delay the delivery of that therapy, according to the nature of the respective distinct patient-initiated signal produced by such passing of the magnet over the housing. For example, a reed switch within the housing detects a sequence of magnet passes over the housing, to trigger the particular response.

Circumstances under which a patient might choose to postpone a discomforting atrial defibriliating shock might include, for example, being the sole driver on an automobile trip extending, say, one, two, or more hours when made aware that atrial fibrillation is occurring by muscle twitching induced by the implanted device. The patient might wish either to complete a shorter trip, or to pull over to the side of the road or into a parking area, to accept the shock when the car is parked to avoid the possibility of losing control while the vehicle is moving. Or the patient might be at a dinner party, and choose to excuse herself to lie down when the shock is delivered. In each of these types of circumstances, the patient is able to select the more opportune time for the defibrillating shock to be delivered by initiating it through a tapping on generator case 15 with a distinct coded pattern that is preset to produce that result. A fail-safe measure may be implemented by the programming of the device to assure that if the patient does not initiate the shock within a predetermined time interval following the onset of atrial fibrillation, the device itself will automatically do so when that interval elapses. The automatic delivery would be aborted if the shock were initiated by the patient before the interval times out, or if a spontaneous cessation of the dysrhythmia has occurred by the time the interval times out.

In addition to the advantage that the patient may choose a more relaxed state for administering the shock, medication such as diazepam or metazolam tablets may be taken to produce slight sedation so as to reduce the pain accompanying the shock delivery. Additionally, the patient may take an antiarrhythmic medication such as sotalol or amiodarone which have been shown to have beneficial effect in reducing the acute threshold energy level to be reached by the shock in order to produce defibrillation.

Figure 5:
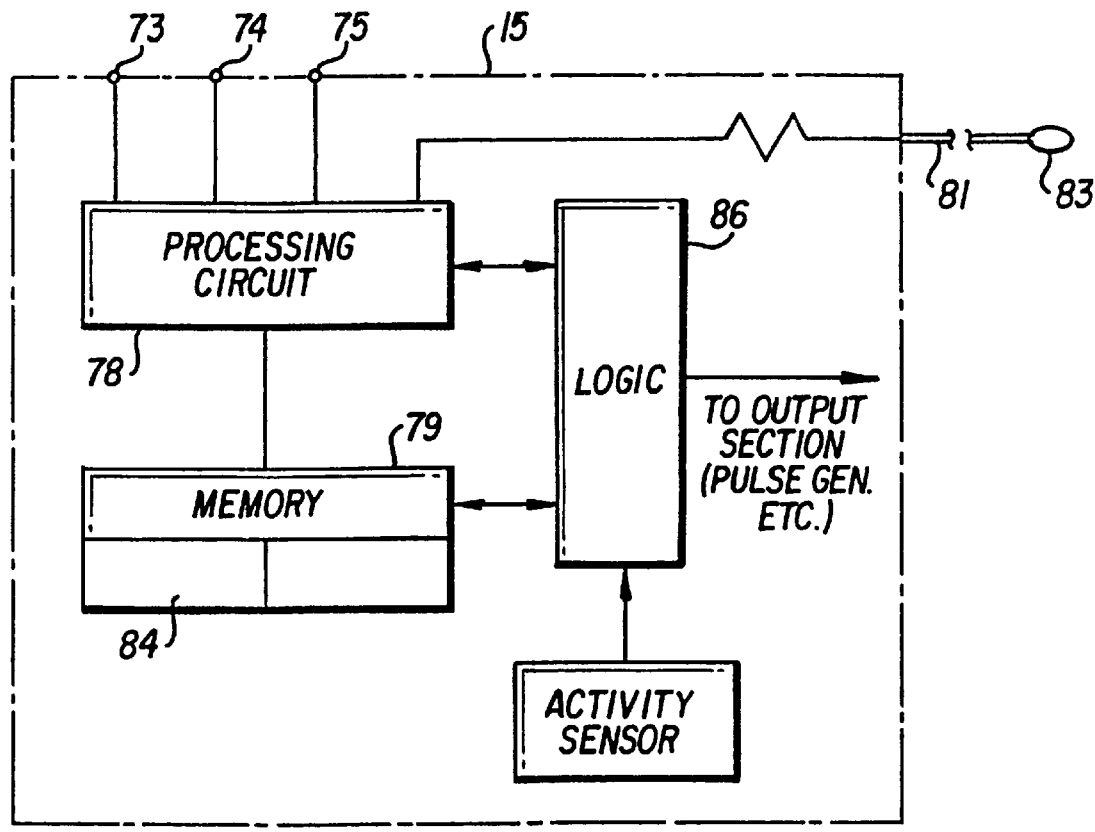
FIG. 5 is a block diagram of an exemplary rate-adaptive pacemaker utilizing the features of the invention.

The components of the pacemaker are illustrated in FIG. 5. The intracardiac signals are detected using a bipolar arrangement with lead 81 and electrode 83, and case 15. These signals are digitally stored in a memory 79 after analysis by a processing circuit 78. Preferably, from five to ten minutes of real-time lead ECG information is stored.

In addition, the two or three dot electrodes 73, 74, 75 in the header of the signal generator detect the ECG signal much as a surface ECG would be detected, except that here the electrodes are disposed just below the skin rather than on the skin of the patient. The signal information may be indicative of and used to alert the patient of a detected malfunction in the implanted pacemaker. For example, the surface-mounted electrodes may detect an appropriate ECG signal, while the lead-based electrodes may indicate a weak signal or none at all. In those circumstances the indication is that the lead may be fractured because the signal is lost. In response, the patient is alerted to the malfunction by means of stimulation of the pectoral (or other) muscle with voltages ranging from 2.0 to 7.5 volts. By recognizing this muscle twitch, the patient recognizes the existence of a malfunction, as an indication to seek out the nearest physician, or to use conventional transtelephonic monitoring of the implanted pacemaker to detect the source of the problem.

It is desirable to store real-time ECG information from the electrodes, particularly the surface-mounted ones, to enable interpretation and analysis of the problem by the physician. With current pacemaker memory capability, however, only a period of about ten minutes of real-time ECG can be stored. In a preferred embodiment, the signal is digitally stored using a first in/first out technique in which a moving window or loop is used in which the window is held open over the entire 10-minute interval, and the last minute of the interval is discarded as the next minute is stored. If the pacemaker detects a rapid and unusual change in function, such as a diagnosis of mode switch (a change of modes) following rapid atrial arrhythmias, it can preserve this moment of interest and the actual time of occurrence by storage in the device memory. An auto-diagnostic event triggering occurs for periods of interest that are of importance for a review and analysis by a physician to identify whether the implanted pacemaker was performing at the time in accordance with its incorporated decision rules as implemented/programmed in the device. In the case of an atrial mode switch, for example, the criteria is a particular number of atrial beats exceeding a predetermined rate. It is desirable and helpful to identify each period for which such triggering occurs within the memory itself, and to observe the real-time ECG obtained from the pacemaker leads as well as the body ECG derived from the surface-mounted electrodes for the same interval of interest.

In an alternative method of memory storage, some portion of the ECG information is frozen and stored for a longer period of time than previously, and in which the memory storage is initiated by the patient by tapping on the case in another distinct sequence especially coded for that event. The accelerometer-driven pacer, for example, is struck at a certain characteristic staccato to prompt the storage instruction. The signal content in the loop (window) is stored in memory to be available for analysis by the patient's physician during follow-up, and the logic circuit 86 together with timing information supplied by an internal clock locks this moment of interest into longer term memory 84 for the intracardiac signal.

This surface-mounted electrodes-derived ECG is independent of the lead-based intracardiac ECG, and both are transmitted via the telemetry link to an external console (not shown) and recorded on a strip-chart recorder. The transmission of both helps to facilitate the diagnosis of a possible lead or device failure and to enhance the differentiation between a pacemaker-based problem and a heart-based problem, and is achieved by transmission of the two in parallel.

Although a presently contemplated best mode of practicing the invention has been described herein, it will be recognized by those skilled in the art to which the invention pertains from a consideration of the foregoing description, that variations and modifications may be made without departing from the true spirit and scope of the invention. Accordingly, it is intended that the invention shall be limited only by the appended claims and the rules and principles of applicable law.

What is claimed is:

1. A body implantable interventional medical device having a capability to sense cardiac dysrhythmias and to selectively respond with one among a hierarchy of therapies appropriate to terminate the sensed dysrhythmia and return the heart of the patient in whom the device is adapted to be implanted to normal sinus rhythm, said device comprising:

a therapy generator including a housing and means for conducting bidirectional communication with the patient, said bidirectional communication means including:

detection means responsive to occurrence of a predetermined dysrhythmia for alerting the patient of such occurrence, said detection means including electrode means mounted on the device housing for both detecting occurrence of said predetermined dysrhythmia and for alerting the patient thereof, and initiation means responsive to instructions from the patient following such alert for addressing the detected predetermined dysrhythmia.

2. The device of claim 1, wherein said device housing includes a case and a header, and said electrode means includes first and second electrodes mounted on opposite sides of the header to detect cardiac signals that spread through the patient's body tissue and to stimulate the body tissue when cardiac signals indicative of said predetermined dysrhythmia are detected.

3. The device of claim 1, wherein said initiation means includes sensing means for sensing patient-initiated coded signals and for responding thereto by at least one of (i) storing cardiac signals indicative of said predetermined dysrhythima, (ii) deliver a therapy appropriate to terminate said predetermined dysrhythmia, or delaying delivery of said therapy, according to the nature of the patient-initiated coded signals.

4. The device of claim 3, wherein said sensing means comprises means responsive to a predetermined sequence of taps delivered to the device housing.

5. The device of claim 3, wherein said sensing means comprises means responsive to application of a magnetic field adjacent to the device housing.

6. The device of claim 4, wherein said sensing means comprises means responsive separately to first, second, and third predetermined distinct and different coded sequences of taps for storing said cardiac signals, for delivering said appropriate therapy, and for delaying delivery of said appropriate therapy, respectively.

7. The device of claim 1, detection means further comprises an acoustic source within said housing activated by said electrode means for sounding an audible alert to the patient.

8. The device of claim 1, wherein said initiation means comprises means for triggering diagnostic functions of the device.

9. The device of claim 1, wherein said initiation means comprises means for triggering therapeutic functions of the device.

10. A body implantable interventional medical device having a capability to sense cardiac dysrhythmias and to selectively respond with one among a hierarchy of therapies appropriate to terminate the sensed dysrhythmia and return the heart of the patient in whom the device is adapted to be implanted to normal sinus rhythm, said device comprising:

a therapy generator including a housing and means for conducting bidirectional communication with the patient, said bidirectional communication means including:
  detection means responsive to occurrence of a predetermined dysrhythmia for alerting the patient of such occurrence, and
  initiation means responsive to instructions from the patient following such alert for addressing the detected predetermined dysrhythmia; and
means responsive to detection of said predetermined dysrhythmia to open a preset time window, and mews responsive during the time window to patient-initiated signals for triggering a therapeutic function of the device and to closing of the time window for reversion to automatic therapy delivery by the device.

11. An implantable interventional medical device for treating cardiac dysrhythmias, comprising electronic components and circuitry for performing diagnostic and therapeutic functions with respect to said cardiac dyshythmias, a case housing said electronic components and circuitry an electrical connector attached to the case and connected to said circuitry for conducting electrical signals to and from said circuitry representing detected cardiac signals for diagnosing dysrhythmias and electrical stimuli for delivery of therapy in response to such diagnosis respectively, an accelerometer mounted in said case for both (i) detecting physical activity of the patient in whom the device is to be implanted to control cardiac pacing functions of said device and (ii) responding to coded taps on said case representing instructions to said circuitry to initiate at least some of said diagnostic and therapeutic functions of said device, and means for overriding an instruction represented by said coded taps to delay delivery of a therapeutic function of said device when the delay exceeds a predetermined time interval.

12. In a body implantable interventional medical device having a capability to sense cardiac dysrhythmias and to selectively respond with any among a hierarchy of therapies appropriate to terminate the sensed dysrhythmia and return the heart of the patient in whom the device is adapted to be implanted to normal sinus rhythm, a device-implemented method of bidirectional communication with the patient comprising the steps of detecting the occurrence of any one among a set of predetermined dysrhythmias, responding to the detection of a non-life threating dysrhythmia among set by alerting the patient thereof, responding to patient-initiated coded signals applied as instructions to said device following such alert for mandating one among a plurality of patient directives in response to said detected dysrhythmia wherein said plurality includes directing a delay in delivery of therapy which would otherwise be a response by said device to said detected dysrhythmia and overriding a patient directive to delay delivery of therapy after said delay exceeds a predetermined time interval while said detected dysrhythmia is still occurring.

13. The device-implemented method of claim 12, including sensing said patient-initiated coded signals, and wherein said patient directives in response thereto include at least one of (i) storing cardiac signals indicative of the detected dysrhythmia or (ii) delivering a therapy appropriate to terminate said detected dysrhythmia or (iii) postponing delivery of said therapy, according to the nature of the patient-initiated coded signals.

14. The device-implemented method of claim 13, including sensing patient-initiated coded signals in the form of a predetermined sequence of taps delivered to the device housing.

15. The device-implemented method of claim 13, including sensing patient-initiated coded signals in the form of magnet induce d-actuation imposed on the device housing.

16. The device-implemented method of claim 12, including energizing electrodes surface-mounted on a housing for the device to alert the patient of said detected dysrhythmia.

17. The device-implemented method of claim 12, including energizing an acoustic source within a housing for the device to sound an audible alert to the patient.

18. The device-implemented method of claim 12, including responding to said patient-initiated coded signals by triggering diagnostic functions of the device.

19. The device-implemented method of claim 12, including responding to said patient-initiated coded signals by triggering therapeutic functions of the device.

20. In a body implantable interventional medical device having a capability to sense cardiac dysrhythmias and to selectively respond with any among a hierarchy of therapies appropriate to terminate the sensed dysrhythmia and return the heart of the patient in whom the device is adapted to be implanted to normal sinus rhythm, a device-implemented method of bidirectional communication with the patient comprising detecting the occurrence of a predetermined dysrhythmia alerting the patient of said occurrence responding to instructions initiated by the patient following such alert for addressing the detected predetermined dysrhythmia responding to detection of said predetermined dysrhythmia by opening a preset time window, responding during the time window to patient-initiated signals for triggering a therapeutic function of the device, and responding to closing of the time window by reverting to automatic therapy delivery by the device.

* * * * *